United States Patent
Li et al.

(10) Patent No.: US 11,525,774 B2
(45) Date of Patent: Dec. 13, 2022

(54) SENSORY EVALUATION METHOD FOR SPECTRAL DATA OF MAINSTREAM SMOKE

(71) Applicant: CHINA TOBACCO YUNNAN INDUSTRIAL CO., LTD, Kunming (CN)

(72) Inventors: Chao Li, Kunming (CN); Duoqing Fan, Kunming (CN); Mingfeng Wang, Kunming (CN); Hui Wang, Kunming (CN); Exian Li, Kunming (CN); Wen Xiong, Kunming (CN); Ling Ye, Kunming (CN); Fangrui Chen, Kunming (CN); Yuling Wei, Kunming (CN)

(73) Assignee: CHINA TOBACCO YUNNAN INDUSTRIAL CO., LTD, Kunming (CN)

( * ) Notice: Subject to any disclaimer, the term of this patent is extended or adjusted under 35 U.S.C. 154(b) by 0 days.

(21) Appl. No.: 17/595,852

(22) PCT Filed: Mar. 4, 2021

(86) PCT No.: PCT/CN2021/079141
§ 371 (c)(1),
(2) Date: Nov. 29, 2021

(87) PCT Pub. No.: WO2021/253874
PCT Pub. Date: Dec. 23, 2021

(65) Prior Publication Data
US 2022/0268696 A1    Aug. 25, 2022

(30) Foreign Application Priority Data
Jan. 14, 2021  (CN) .......................... 202110050500.6

(51) Int. Cl.
*G01N 21/3504*    (2014.01)
*G01N 33/00*    (2006.01)
(Continued)

(52) U.S. Cl.
CPC ..... *G01N 21/3504* (2013.01); *G01N 33/0027* (2013.01); *G06K 9/0051* (2013.01);
(Continued)

(58) Field of Classification Search
CPC .......... G01N 21/3504; G01N 33/0027; G01N 21/031; G01N 2021/052; G01N 2201/129;
(Continued)

(56) References Cited

FOREIGN PATENT DOCUMENTS

CN      1975705 A      6/2007
CN    107014768 A      8/2017
(Continued)

OTHER PUBLICATIONS

Krusemann et al. ("Sensory analysis of characterising flavours: evaluating tobacco product odours using an expert panel," Tobacco Control, vol. 28 (2) pp. 152-160, Mar. 2019) (Year: 2019).*

*Primary Examiner* — David P Porta
*Assistant Examiner* — Meenakshi S Sahu
(74) *Attorney, Agent, or Firm* — Bayramoglu Law Offices LLC

(57) ABSTRACT

A sensory evaluation method for spectral data of mainstream smoke includes: performing a data enhancement on spectral data of mainstream smoke of a plurality of cigarettes; extracting a shallow spectral characteristic from the spectral data of the mainstream smoke of each cigarette; obtaining a shallow sensory quality result of the spectral data of the mainstream smoke of each cigarette based on the spectral data of the mainstream smoke of each cigarette and the shallow spectral characteristic; extracting deep spatial char-
(Continued)

acteristics from the spectral data of the mainstream smoke of each cigarette; obtaining a deep sensory quality result based on the spectral data of the mainstream smoke of each cigarette and the deep spatial characteristics; obtaining a comprehensive sensory quality result according to the shallow sensory quality result and the deep sensory quality result. The sensory evaluation method achieves accurate screening of unknowns in the mainstream smoke.

10 Claims, 1 Drawing Sheet

(51) Int. Cl.
  G06K 9/00 (2022.01)
  G06K 9/62 (2022.01)
  G06N 3/08 (2006.01)
(52) U.S. Cl.
  CPC ....... G06K 9/00536 (2013.01); G06K 9/6269 (2013.01); G06N 3/08 (2013.01)

(58) Field of Classification Search
  CPC ............. G06K 9/0051; G06K 9/00536; G06K 9/6256; G06K 9/6268; G06K 9/6284; G06N 3/02; G06N 3/0454; G06N 20/00; G06N 3/04; G06V 10/82; G06Q 10/06395
  See application file for complete search history.

(56) References Cited

FOREIGN PATENT DOCUMENTS

| | | |
|---|---|---|
| CN | 107646089 A | 1/2018 |
| CN | 108414471 A | 8/2018 |
| CN | 108801968 A | 11/2018 |
| CN | 109444326 A | 3/2019 |
| CN | 110132880 A | 8/2019 |
| JP | H09304371 A | 11/1997 |

\* cited by examiner

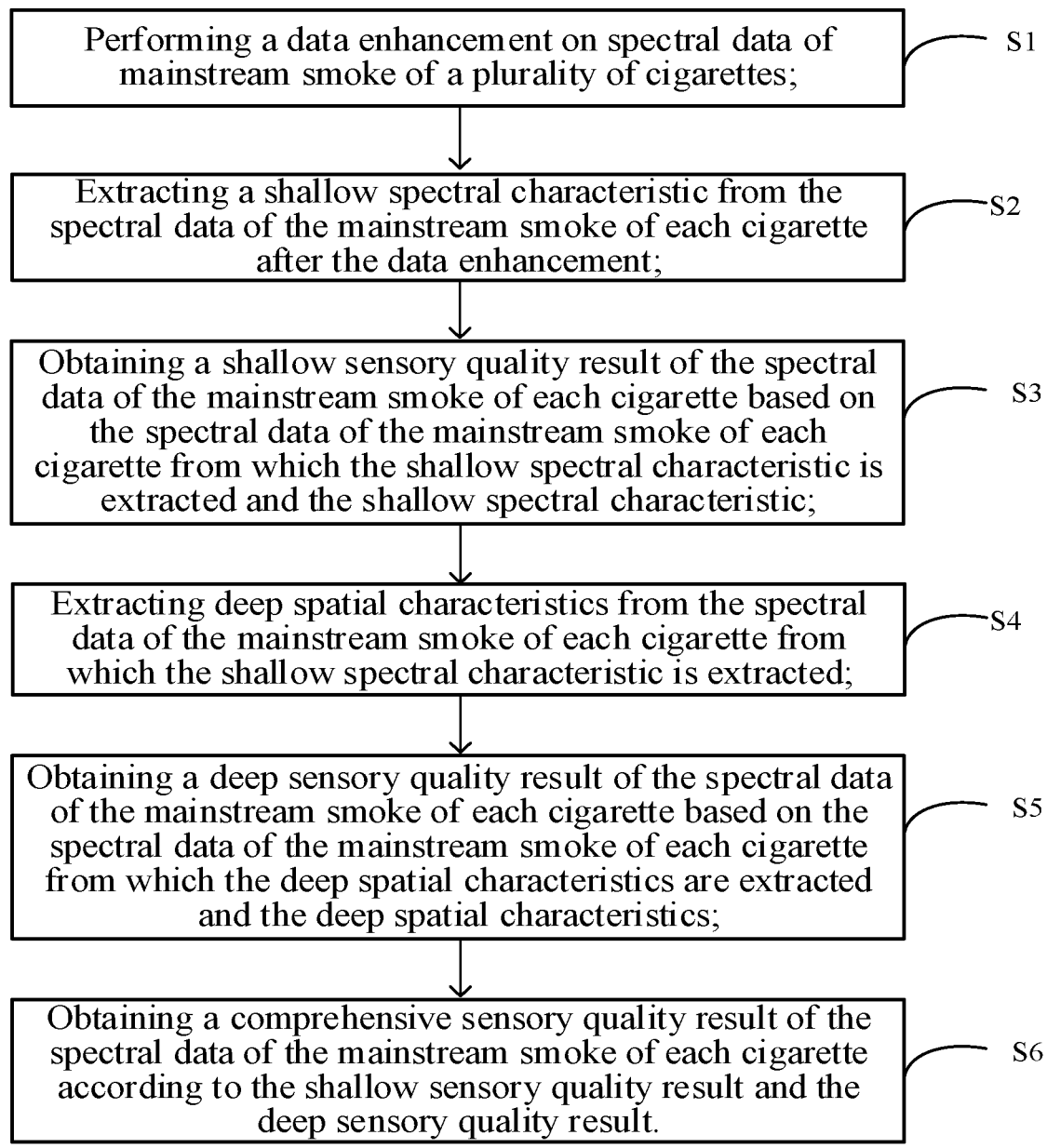

SENSORY EVALUATION METHOD FOR SPECTRAL DATA OF MAINSTREAM SMOKE

CROSS REFERENCE TO THE RELATED APPLICATIONS

This application is the national phase entry of International Application No. PCT/CN2021/079141, filed on Mar. 4, 2021, which is based upon and claims priority to Chinese Patent Application No. 202110050500.6, filed on Jan. 14, 2021, the entire contents of which are incorporated herein by reference.

TECHNICAL FIELD

The present invention relates to the technical field of tobacco quality evaluation, and more particularly, to a sensory evaluation method for spectral data of mainstream smoke.

BACKGROUND

As special consumer goods, the quality and taste of the cigarettes are directly affected by the content of key components in mainstream smoke. To achieve accurate evaluation of cigarettes in the tobacco industry, it is urgent to solve the technical bottleneck of effectively quantifying the correlation between smoke composition and sensory evaluation.

At present, a sensory evaluation method for the spectral data of the mainstream smoke is achieved through expert evaluation, where experts smoke cigarettes and score the corresponding items. This sensory evaluation method relies on manpower and is affected by the experts' own factors and the external environment, which brings uncertain factors to the evaluation results. Meanwhile, this sensory evaluation method is laborious, cumbersome, inefficient and unstable. Therefore, it is highly desirable to develop a reasonable sensory evaluation method for the spectral data of the mainstream smoke.

SUMMARY

In order to solve the problems existing in the prior art, an objective of the present invention is to provide a sensory evaluation method for spectral data of mainstream smoke. The present invention can improve the efficiency, accuracy and stability of sensory evaluation of mainstream smoke.

The present invention provides a sensory evaluation method for spectral data of mainstream smoke, including:

performing a data enhancement on spectral data of mainstream smoke of a plurality of cigarettes;

extracting a shallow spectral characteristic from the spectral data of the mainstream smoke of each cigarette after the data enhancement;

obtaining a shallow sensory quality result of the spectral data of the mainstream smoke of each cigarette based on the spectral data of the mainstream smoke of each cigarette from which the shallow spectral characteristic is extracted and the shallow spectral characteristic;

extracting deep spatial characteristics from the spectral data of the mainstream smoke of each cigarette from which the shallow spectral characteristic is extracted;

obtaining a deep sensory quality result of the spectral data of the mainstream smoke of each cigarette based on the spectral data of the mainstream smoke of each cigarette from which the deep spatial characteristics are extracted and the deep spatial characteristics; and obtaining a comprehensive sensory quality result of the spectral data of the mainstream smoke of each cigarette according to the shallow sensory quality result and the deep sensory quality result.

In the above sensory evaluation method for spectral data of mainstream smoke, preferably, the spectral data of the mainstream smoke may include mid-infrared spectral data.

In the above sensory evaluation method for spectral data of mainstream smoke, preferably, the step of performing the data enhancement on the spectral data of the mainstream smoke of the plurality of cigarettes may include:

performing a horizontal flipping on the spectral data of the mainstream smoke of each cigarette;

performing a random cutting on the spectral data of the mainstream smoke of each cigarette after the horizontal flipping;

performing a physical perturbation on the spectral data of the mainstream smoke of each cigarette after the random cutting; and performing a component perturbation on the spectral data of the mainstream smoke of each cigarette after the physical perturbation.

In the above sensory evaluation method for spectral data of mainstream smoke, preferably, the step of extracting the shallow spectral characteristic from the spectral data of the mainstream smoke of each cigarette after the data enhancement may include:

eliminating an outlier data point from the spectral data of the mainstream smoke of the plurality of cigarettes through a Hotelling $T^2$ statistic of a spectral vector to eliminate outlier data from the spectral data of the mainstream smoke; and performing a denoising on the spectral data of the mainstream smoke of each cigarette from which the outlier data is eliminated, by at least one of a second-order differential, a Karl Norris derivative filter, a multivariate scatter correction (MSC) and a wavelet transform (WT).

In the above sensory evaluation method for spectral data of mainstream smoke, preferably, the step of obtaining the shallow sensory quality result of the spectral data of the mainstream smoke of each cigarette based on the spectral data of the mainstream smoke of each cigarette from which the shallow spectral characteristic is extracted and the shallow spectral characteristic may include:

inputting the spectral data of the mainstream smoke of each cigarette from which the shallow spectral characteristic is extracted into a first sensory classification model constructed in advance to obtain the shallow sensory quality result of the spectral data of the mainstream smoke of each cigarette.

In the above sensory evaluation method for spectral data of mainstream smoke, preferably, the first sensory classification model may be constructed based on principal component analysis (PCA) in combination with a nonlinear support vector machine (SVM), and a method for constructing the first sensory classification model may include:

performing characteristic selection on the spectral data of the mainstream smoke of each cigarette after the denoising based on the PCA to extract a characteristic peak of each component of the mainstream smoke in the spectral data; and training, based on the nonlinear SVM, the spectral data of the mainstream smoke of each cigarette from which the characteristic peak is extracted, to obtain the first sensory classification model.

In the above sensory evaluation method for spectral data of mainstream smoke, preferably, the step of extracting the deep spatial characteristics from the spectral data of the mainstream smoke of each cigarette from which the shallow spectral characteristic is extracted may include:

extracting, based on a deep residual convolutional neural network (CNN), the deep spatial characteristics from the spectral data of the mainstream smoke of each cigarette from which the shallow spectral characteristic is extracted.

In the above sensory evaluation method for spectral data of mainstream smoke, preferably, the step of obtaining the deep sensory quality result of the spectral data of the mainstream smoke of each cigarette based on the spectral data of the mainstream smoke of each cigarette from which the deep spatial characteristics are extracted and the deep spatial characteristics may include:

inputting a plurality of deep spatial characteristics extracted based on the deep residual CNN into an SVM in a stack manner to obtain a second sensory classification model; and inputting the spectral data of the mainstream smoke of each cigarette from which the deep spatial characteristics are extracted into the second sensory classification model to obtain the deep sensory quality result of the spectral data of the mainstream smoke of each cigarette.

In the above sensory evaluation method for spectral data of mainstream smoke, preferably, a method for determining a network parameter of the deep residual CNN may includes:

based on a fixed spectral data set of the mainstream smoke of each cigarette, taking an optimal classification error as a first objective function to obtain a first optimal network parameter;

taking a maximum computing efficiency as a second objective function to obtain a second optimal network parameter; and selecting a balance point of a convolution kernel size of a first optimal convolution kernel corresponding to the first optimal network parameter and a second optimal convolution kernel corresponding to the second optimal network parameter to be a final network parameter of the deep residual CNN.

In the above sensory evaluation method for spectral data of mainstream smoke, preferably, the step of obtaining the comprehensive sensory quality result of the spectral data of the mainstream smoke of each cigarette according to the shallow sensory quality result and the deep sensory quality result may include:

respectively comparing the shallow sensory quality result and the deep sensory quality result with an expert evaluation result to obtain a shallow modeling accuracy rate corresponding to the shallow sensory quality result and a deep modeling accuracy rate corresponding to the deep sensory quality result;

determining a weight of the shallow sensory quality result and the deep sensory quality result according to the shallow modeling accuracy rate and the deep modeling accuracy rate; and performing a weighted summation on the shallow sensory quality result and the deep sensory quality result to obtain the comprehensive sensory quality result.

The present invention performs data enhancement on the spectral data of the mainstream smoke, which can maximize the spectral and spatial characteristic paradigms implicit in the mainstream smoke in case of limited samples, and effectively reduce the demand for the training sample size. The present invention extracts shallow spectral characteristics to provide guidance information of key components of a complex system for subsequent deep learning, which can improve the extraction accuracy of deep spatial characteristics. The present invention extracts deep spatial characteristics to quickly learn effective deep characteristic representation from training data and enhance the characteristic information expression of abnormal and normal samples. The present invention respectively extracts spectral and spatial characteristics from the shallower to the deeper, and automatically and directly obtains the sensory evaluation results of the mainstream smoke by a fused spectrum-spatial classification framework, so as to achieve accurate screening of unknowns in the mainstream smoke.

BRIEF DESCRIPTION OF THE DRAWINGS

In order to make the objectives, technical solutions and advantages of the present invention clearer, the present invention is described in further detail below with reference to the drawings.

FIGURE is a flowchart of a sensory evaluation method for spectral data of mainstream smoke according to an example of the present invention.

DETAILED DESCRIPTION OF THE EMBODIMENTS

The exemplary embodiments of the present invention are described below with reference to the drawings. The description of the exemplary embodiments is merely illustrative, rather than to limit the present invention and application or use thereof. The present invention may be embodied in many different forms and is not limited to the embodiments set forth herein. These embodiments are provided to make the present invention thorough and complete, and to disclose the scope of the present invention to those skilled in the art. It should be noted that, unless specifically stated otherwise, the relative arrangements of components and steps, material components, numerical expressions and numerical values set forth in these embodiments should be interpreted as merely exemplary rather than limiting.

Terms such as "first" and "second" used herein do not denote any order, quantity or importance, but are merely intended to distinguish between different constituents. Terms "include", "comprise" and other similar words mean that the element before the word is included in the element listed after the word, but it does not exclude the possibility that other element is also covered. Terms such as "Upper" and "lower" are used only to indicate a relative positional relationship, and when the absolute position of the described object is changed, the relative positional relationship is changed accordingly.

In the present invention, when it is described that a specific component is located between a first component and a second component, there may or may not be an intermediate component between the specific component and the first component or the second component. When it is described that a specific component is connected to another component, the specific component may be directly connected to another component without an intermediate component, or may be indirectly connected to another component through an intermediate component.

Unless specifically defined otherwise, all terms (including technical or scientific terms) used in the present invention have the same meaning as understood by those of ordinary skill in the art to which the present invention belongs. It should also be understood that, unless expressly required, the terms defined in a general dictionary should be interpreted as having meanings consistent with their meanings in the context of related art, and should not be interpreted with idealized or extremely formal meanings.

The technologies, methods and equipment known to those of ordinary skill in the related art may not be discussed in detail, but where appropriate, the technologies, methods and equipment should be regarded as part of the specification.

An example of the present invention provides a sensory evaluation method for spectral data of mainstream smoke. As shown in FIGURE, the method includes:

S1: Perform data enhancement on spectral data of mainstream smoke of a plurality of cigarettes.

The spectral data of the mainstream smoke includes mid-infrared spectral data. The spectral data is specifically acquired based on hollow-core waveguide two-dimensional (2D) infrared spectroscopy. Compared with conventional infrared spectroscopy, hollow-core waveguide infrared spectroscopy is used as an infrared enhancement technology. The hollow-core fiber technology relies on the high reflectivity of the Ag/AgI composite coating to cause the incident light to form multiple reflections in the hollow-core fiber to extend the optical path for the interaction between light and matter. It can more efficiently increase the infrared absorption intensity of the system to be tested, thereby reducing the detection limit and improving the precision and accuracy of the analysis.

The enhancement processing of the spectral data of the mainstream smoke can reduce the requirement for the number of training samples from the perspective of global optimization, and enhance the spatial paradigm of the spectra (for example, hollow-core waveguide 2D infrared spectra) of components related to the mainstream smoke. It can effectively reduce the risk of overfitting between a first sensory classification model and a second sensory classification model (to be described later). In this way, this step can maximize the spectral and spatial characteristic paradigms implicit in the mainstream smoke in case of limited samples, and promote the second sensory classification model to deeply mine existing data, effectively reducing the demand for the training sample size.

Further, in an implementation of the sensory evaluation method for spectral data of mainstream smoke, step S1 may specifically include:

S11: Perform a horizontal flipping on the spectral data of the mainstream smoke of each cigarette.

S12: Perform a random cutting on the spectral data of the mainstream smoke of each cigarette after the horizontal flipping.

Since the part involving deep learning in the second sensory classification model requires the highest amount of data, the spatial distribution characteristic in the hollow-core waveguide 2D infrared spectral data can be regarded as image information. Therefore, the present invention adopts the traditional image enhancement mode to horizontally flip and randomly cut the data, so as to improve the effectiveness and robustness of the second sensory classification model for spatial image recognition.

S13: Perform a physical perturbation on the spectral data of the mainstream smoke of each cigarette after the random cutting.

In the analysis of hollow-core waveguide 2D infrared spectroscopy of the actual sample, the 2D spectral information is affected by the material composition information and its physical state. Therefore, by changing the physical state of the sample, more information about the paradigm of hollow-core waveguide 2D infrared spectroscopy can be effectively acquired, thereby improving the accuracy and effectiveness of deep learning. The physical perturbation factors in the mainstream smoke include the influence of different physical states such as temperature, wind speed, pressure and extraction method on the hollow-core waveguide 2D infrared spectral information of the mainstream smoke.

S14: Perform a component perturbation on the spectral data of the mainstream smoke of each cigarette after the physical perturbation.

In a specific implementation, by randomly adding standard samples of different formulas, changing the composition of the formula and by other component perturbation methods, the changes in the hollow-core waveguide 2D infrared spectral information of the mainstream smoke under different component perturbations can be determined.

Through the above different data enhancement methods, the paradigm information of the hollow-core waveguide 2D infrared spectral signal of the actual sample can be improved, and then the classification and recognition performance of the subsequent hollow-core waveguide 2D infrared spectrum can be improved.

S2: Extract a shallow spectral characteristic from the spectral data of the mainstream smoke of each cigarette after the data enhancement.

Further, in an implementation of the sensory evaluation method for spectral data of mainstream smoke, step S2 may specifically include:

S21: Eliminate an outlier data point from the spectral data of the mainstream smoke of the plurality of cigarettes through a Hotelling $T^2$ statistic of a spectral vector to eliminate outlier data from the spectral data of the mainstream smoke.

S22: Perform a denoising on the spectral data of the mainstream smoke of each cigarette from which the outlier data is eliminated, by at least one of a second-order differential, a Karl Norris derivative filter, a multivariate scatter correction (MSC) and a wavelet transform (WT).

The denoising can reduce noise interference, make the characteristic peaks in the spectral data of the mainstream smoke more obvious, and facilitate the extraction of the characteristic peaks from the background in the spectral data of the mainstream smoke, thereby improving the signal-to-noise ratio (SNR). Moreover, through data screening and denoising, it is convenient for a subsequent spectral analysis method to accurately extract the data characteristics of the substance to be tested.

S3: Obtain a shallow sensory quality result of the spectral data of the mainstream smoke of each cigarette based on the spectral data of the mainstream smoke of each cigarette from which the shallow spectral characteristic is extracted and the shallow spectral characteristic.

The purpose of extracting the shallow spectral characteristic is to extract the spectral characteristic of the key components of the sample from the complex and changing spectral signal (for example, the hollow-core waveguide 2D infrared spectrum), and to reduce the dimensionality of the spectrum. Specifically, the spectral data of the mainstream smoke of each cigarette from which the shallow spectral characteristic is extracted is input into a first sensory classification model constructed in advance to obtain the shallow sensory quality result of the spectral data of the mainstream smoke of each cigarette. The extraction of the shallow spectral characteristic can provide guidance information of key components of the complex system for subsequent deep learning, thereby improving the accuracy of deep spatial characteristic extraction.

Further, the first sensory classification model is constructed based on principal component analysis (PCA) in combination with a nonlinear support vector machine (SVM), and a method for constructing the first sensory classification model includes:

Perform characteristic selection on the spectral data of the mainstream smoke of each cigarette after the denoising based on the PCA to extract a characteristic peak of each component of the mainstream smoke in the spectral data.

Train, based on the nonlinear SVM, the spectral data of the mainstream smoke of each cigarette from which the characteristic peak is extracted, to obtain the first sensory classification model.

Compared with a linear SVM, the classification process of the nonlinear SVM is more ambiguous. As long as the extracted characteristic peak is input, a discriminant relationship and a classification relationship are established automatically.

Further, the classification result of the first sensory classification model includes at least good, fair and poor. It should be noted that the present invention does not specifically limit the classification results and quantity of the first sensory classification model, and other classification results can be obtained by defining parameters and changing the weights.

Further, the first sensory classification model uses an expert sensory evaluation score to supervise a first classification determination value output by the first sensory classification model during the training process, so as to realize the verification and update of the first sensory classification model.

In an implementation of the sensory evaluation method for spectral data of mainstream smoke, the first sensory classification model is trained as follows:

First, a training set of the spectral data of the mainstream smoke is input to the first sensory classification model. Specifically, it may include: remove outlier data in an original training set of the spectral data of the mainstream smoke of each cigarette; performing a denoising on the spectral data of the mainstream smoke of each cigarette in the original training set from which the outlier data is eliminated; and input the spectral data of the mainstream smoke of each cigarette in the original training set after the denoising into the first sensory classification model.

Then, according to the first classification determination value and the expert sensory evaluation score, a first objective function is obtained, and a gradient of the first objective function is transmitted back to the first sensory classification model.

Finally, when a value of the first objective function obtained based on the first classification determination value and the expert sensory evaluation score reaches a set value, the training is stopped.

S4: Extract deep spatial characteristics from the spectral data of the mainstream smoke of each cigarette from which the shallow spectral characteristic is extracted.

Specifically, based on a deep residual convolutional neural network (CNN), the deep spatial characteristics are extracted from the spectral data of the mainstream smoke of each cigarette from which the shallow spectral characteristic is extracted. When an unknown interference appears in the complex system, the spatial topology information of the original key components will cause distortion. The deep residual CNN can quickly learn effective deep characteristic representation from training data in response to this change, and enhance the characteristic information expression of abnormal and normal samples.

S5: Obtain a deep sensory quality result of the spectral data of the mainstream smoke of each cigarette based on the spectral data of the mainstream smoke of each cigarette from which the deep spatial characteristics are extracted and the deep spatial characteristics.

The purpose of extracting the deep spatial characteristics is to use the deep residual CNN to complete the extraction and enhancement of the deep spatial characteristics in a translation-invariant way. A method for determining a network parameter of the deep residual CNN includes:

Based on a fixed spectral data set of the mainstream smoke of each cigarette, take an optimal classification error as a first objective function to obtain a first optimal network parameter.

Take a maximum computing efficiency as a second objective function to obtain a second optimal network parameter.

Select a balance point of a convolution kernel size of a first optimal convolution kernel corresponding to the first optimal network parameter and a second optimal convolution kernel corresponding to the second optimal network parameter to be a final network parameter of the deep residual CNN.

Further, in an implementation of the sensory evaluation method for spectral data of mainstream smoke, step S5 may specifically include:

S51: Input a plurality of deep spatial characteristics extracted based on the deep residual CNN into an SVM in a stack manner to obtain a second sensory classification model.

Further, the classification result of the second sensory classification model is a sensory score. It should be noted that the present invention does not specifically limit the classification results and quantity of the second sensory classification model, and other classification results can be obtained by defining parameters and changing the weights.

S52: Input the spectral data of the mainstream smoke of each cigarette from which the deep spatial characteristics are extracted into the second sensory classification model to obtain the deep sensory quality result of the spectral data of the mainstream smoke of each cigarette.

The present invention introduces a deep learning strategy to simulate the sensory evaluation process of different experts. In a specific implementation, in the deep learning process, the present invention divides the objective problem of analyzing sensory data of a single cigarette through mainstream smoke into a multi-classification problem configured with a predictive model with different weights and parameters to simulate the sensory differences of different experts. The present invention regards the mainstream smoke components of different cigarette samples as a multi-label problem based on the prior knowledge of experts, and uses the expert-labeled score information obtained by the evaluation of human experts to improve the supervision information of the deep learning model. In the process of label improvement, the symbiotic relationship between the score information obtained through the second sensory classification model and the expert-labeled score information obtained through human expert evaluation is used to improve the obtained deep learning training result.

Further, the present invention selects standard cigarette samples with different distinguishing qualities. The present invention acquires the hollow-core waveguide 2D infrared spectral information of the samples as an input into the second sensory classification model to perform sensory evaluation and analysis on the mainstream smoke. The present invention compares the obtained results with expert scores to determine the effectiveness of the second sensory classification model. In this way, through repeated iterations and upgrades, the present invention can analyze the characteristics of the hollow-core waveguide 2D infrared spectral data and its inherent laws when it is difficult to establish an accurate evaluation model. In this way, the present invention can perform local dynamic analysis in the characteristic segment related to sensory evaluation, and adaptively approach the objective function, thereby realizing the quality evaluation and sensory analysis of the mainstream smoke.

S6: Obtain a comprehensive sensory quality result of the spectral data of the mainstream smoke of each cigarette according to the shallow sensory quality result and the deep sensory quality result.

Further, in an implementation of the sensory evaluation method for spectral data of mainstream smoke, step S6 may specifically include:

S61: Respectively compare the shallow sensory quality result and the deep sensory quality result with an expert evaluation result to obtain a shallow modeling accuracy rate corresponding to the shallow sensory quality result and a deep modeling accuracy rate corresponding to the deep sensory quality result.

S62: Determine a weight of the shallow sensory quality result and the deep sensory quality result according to the shallow modeling accuracy rate and the deep modeling accuracy rate.

S63: Perform a weighted summation on the shallow sensory quality result and the deep sensory quality result to obtain the comprehensive sensory quality result.

The present invention obtains the comprehensive sensory quality result based on the shallow sensory quality result and the deep sensory quality result, and organically combines the characteristics between the spectral shallow characteristic network and the deep characteristic network, which complement and correct each other. Therefore, the present invention has outstanding capabilities of extracting spectral big data characteristics.

The present invention performs data enhancement on the spectral data of the mainstream smoke, which can maximize the spectral and spatial characteristic paradigms implicit in the mainstream smoke in case of limited samples, and effectively reduce the demand for the training sample size. The present invention extracts shallow spectral characteristics to provide guidance information of key components of a complex system for subsequent deep learning, which can improve the extraction accuracy of deep spatial characteristics. The present invention extracts deep spatial characteristics to quickly learn effective deep characteristic representation from training data and enhance the characteristic information expression of abnormal and normal samples. The present invention respectively extracts spectral and spatial characteristics from the shallower to the deeper, and automatically and directly obtains the sensory evaluation results of the mainstream smoke by a fused spectrum-spatial classification framework, so as to achieve accurate screening of unknowns in the mainstream smoke.

The embodiments of the present invention are described in detail above. In order to avoid obscuring the concept of the present invention, some details known in the art are not described. Those skilled in the art can fully understand how to implement the technical solutions disclosed herein based on the above description.

Although some specific embodiments of the present invention are described in detail through examples, those skilled in the art should understand that the above examples are only for illustration and not for limiting the scope of the present invention. Those skilled in the art should understand that the above embodiments can be modified or some technical characteristics can be equivalently replaced without departing from the scope and spirit of the present invention. The scope of the present invention is defined by the appended claims.

What is claimed is:

1. A sensory evaluation method for spectral data of mainstream smoke, comprising:
    performing a data enhancement on spectral data of mainstream smoke of each cigarette of a plurality of cigarettes;
    extracting a shallow spectral characteristic from the spectral data of the mainstream smoke of each cigarette after the data enhancement;
    obtaining a shallow sensory quality result of the spectral data of the mainstream smoke of each cigarette based on the spectral data of the mainstream smoke of each cigarette from which the shallow spectral characteristic is extracted and the shallow spectral characteristic;
    extracting deep spatial characteristics from the spectral data of the mainstream smoke of each cigarette from which the shallow spectral characteristic is extracted;
    obtaining a deep sensory quality result of the spectral data of the mainstream smoke of each cigarette based on the spectral data of the mainstream smoke of each cigarette from which the deep spatial characteristics are extracted and the deep spatial characteristics; and
    obtaining a comprehensive sensory quality result of the spectral data of the mainstream smoke of each cigarette according to the shallow sensory quality result and the deep sensory quality result.

2. The sensory evaluation method for the spectral data of the mainstream smoke according to claim 1, wherein the spectral data of the mainstream smoke comprises mid-infrared spectral data.

3. The sensory evaluation method for the spectral data of the mainstream smoke according to claim 1, wherein the step of performing the data enhancement on the spectral data of the mainstream smoke of each cigarette of the plurality of cigarettes comprises:
    performing a horizontal flipping on the spectral data of the mainstream smoke of each cigarette;
    performing a random cutting on the spectral data of the mainstream smoke of each cigarette after the horizontal flipping;
    performing a physical perturbation on the spectral data of the mainstream smoke of each cigarette after the random cutting; and
    performing a component perturbation on the spectral data of the mainstream smoke of each cigarette after the physical perturbation.

4. The sensory evaluation method for the spectral data of the mainstream smoke according to claim 1, wherein the step of extracting the shallow spectral characteristic from the spectral data of the mainstream smoke of each cigarette after the data enhancement comprises:
    eliminating an outlier data point from the spectral data of the mainstream smoke of each cigarette of the plurality of cigarettes through a Hotelling $T^2$ statistic of a spectral vector to eliminate outlier data from the spectral data of the mainstream smoke; and
    performing a denoising on the spectral data of the mainstream smoke of each cigarette from which the outlier data is eliminated, by at least one of a second-order differential, a Karl Norris derivative filter, a multivariate scatter correction (MSC) and a wavelet transform (WT).

5. The sensory evaluation method for the spectral data of the mainstream smoke according to claim 4, wherein the step of obtaining the shallow sensory quality result of the spectral data of the mainstream smoke of each cigarette based on the spectral data of the mainstream smoke of each cigarette from which the shallow spectral characteristic is extracted and the shallow spectral characteristic comprises:

inputting the spectral data of the mainstream smoke of each cigarette from which the shallow spectral characteristic is extracted into a first sensory classification model constructed in advance to obtain the shallow sensory quality result of the spectral data of the mainstream smoke of each cigarette.

6. The sensory evaluation method for the spectral data of the mainstream smoke according to claim 5, wherein the first sensory classification model is constructed based on principal component analysis (PCA) in combination with a nonlinear support vector machine (SVM), and a method for constructing the first sensory classification model comprises:

performing characteristic selection on the spectral data of the mainstream smoke of each cigarette after the denoising based on the PCA to extract a characteristic peak of each component of the mainstream smoke in the spectral data; and training, based on the nonlinear SVM, the spectral data of the mainstream smoke of each cigarette from which the characteristic peak is extracted, to obtain the first sensory classification model.

7. The sensory evaluation method for the spectral data of the mainstream smoke according to claim 1, wherein the step of extracting the deep spatial characteristics from the spectral data of the mainstream smoke of each cigarette from which the shallow spectral characteristic is extracted comprises:

extracting, based on a deep residual convolutional neural network (CNN), the deep spatial characteristics from the spectral data of the mainstream smoke of each cigarette from which the shallow spectral characteristic is extracted.

8. The sensory evaluation method for the spectral data of the mainstream smoke according to claim 7, wherein the step of obtaining the deep sensory quality result of the spectral data of the mainstream smoke of each cigarette based on the spectral data of the mainstream smoke of each cigarette from which the deep spatial characteristics are extracted and the deep spatial characteristics comprises:

inputting a plurality of deep spatial characteristics extracted based on the deep residual CNN into an SVM in a stack manner to obtain a second sensory classification model; and inputting the spectral data of the mainstream smoke of each cigarette from which the deep spatial characteristics are extracted into the second sensory classification model to obtain the deep sensory quality result of the spectral data of the mainstream smoke of each cigarette.

9. The sensory evaluation method for the spectral data of the mainstream smoke according to claim 7, wherein a method for determining a network parameter of the deep residual CNN comprises:

based on a fixed spectral data set of the mainstream smoke of each cigarette, taking an optimal classification error as a first objective function to obtain a first optimal network parameter;

taking a maximum computing efficiency as a second objective function to obtain a second optimal network parameter; and selecting a balance point of a convolution kernel size of a first optimal convolution kernel corresponding to the first optimal network parameter and a second optimal convolution kernel corresponding to the second optimal network parameter to be a final network parameter of the deep residual CNN.

10. The sensory evaluation method for the spectral data of the mainstream smoke according to claim 1, wherein the step of obtaining the comprehensive sensory quality result of the spectral data of the mainstream smoke of each cigarette according to the shallow sensory quality result and the deep sensory quality result comprises:

respectively comparing the shallow sensory quality result and the deep sensory quality result with an expert evaluation result to obtain a shallow modeling accuracy rate corresponding to the shallow sensory quality result and a deep modeling accuracy rate corresponding to the deep sensory quality result;

determining a weight of the shallow sensory quality result and the deep sensory quality result according to the shallow modeling accuracy rate and the deep modeling accuracy rate; and performing a weighted summation on the shallow sensory quality result and the deep sensory quality result to obtain the comprehensive sensory quality result.

\* \* \* \* \*